(12) United States Patent
Lyren (10) Patent No.: US 10,149,765 B1
(45) Date of Patent: Dec. 11, 2018

(54) HIP IMPLANT WITH POROUS BODY

(71) Applicant: Four Mile Bay, LLC, Wadsworth, OH (US)

(72) Inventor: Philip Scott Lyren, Hong Kong (CN)

( * ) Notice: Subject to any disclaimer, the term of this patent is extended or adjusted under 35 U.S.C. 154(b) by 0 days.

(21) Appl. No.: 15/065,917

(22) Filed: Mar. 10, 2016

Related U.S. Application Data (63) Continuation of application No. 14/461,482, filed on Aug. 18, 2014, now Pat. No. 9,283,080, which is a continuation of application No. 13/592,349, filed on Aug. 23, 2012, now Pat. No. 8,821,582, which is a continuation-in-part of application No. 11/409,611, filed on Apr. 24, 2006, now Pat. No. 8,506,642, which is a continuation of application No. 10/446,069, filed on May 27, 2003, now abandoned.

(51) Int. Cl.
    *A61B 17/72* (2006.01)
    *A61F 2/36* (2006.01)
    *A61F 2/30* (2006.01)
    *A61F 2/28* (2006.01)

(52) U.S. Cl.
    CPC ........ *A61F 2/3672* (2013.01); *A61F 2/30767* (2013.01); *A61F 2/367* (2013.01); *A61F 2/3609* (2013.01); *A61F 2002/2817* (2013.01); *A61F 2002/30013* (2013.01); *A61F 2002/3092* (2013.01); *A61F 2002/30158* (2013.01)

(58) Field of Classification Search
    CPC .............................. A61F 2/36–2/3676; A61F 2002/3678–2002/3698; A61B 17/72–17/7291
    See application file for complete search history.

(56) References Cited

U.S. PATENT DOCUMENTS

| | | | | |
|---|---|---|---|---|
| 3,906,550 A | * | 9/1975 | Rostoker | A61B 17/72 29/419.1 |
| 4,406,023 A | * | 9/1983 | Harris | A61F 2/30767 623/10 |
| 4,608,055 A | * | 8/1986 | Morrey | A61F 2/30907 623/22.46 |
| 5,015,256 A | * | 5/1991 | Bruce | A61F 2/30723 128/898 |
| 5,018,285 A | * | 5/1991 | Zolman | A61F 2/30907 29/419.1 |
| 5,219,363 A | * | 6/1993 | Crowninshield | A61F 2/30907 623/23.34 |
| 5,314,494 A | * | 5/1994 | Huiskes | A61B 17/8808 623/23.35 |
| 5,514,184 A | * | 5/1996 | Doi | A61F 2/30767 623/23.3 |
| 6,296,667 B1 | * | 10/2001 | Johnson | A61F 2/28 623/23.61 |
| 6,361,566 B1 | * | 3/2002 | Al-Hafez | A61F 2/32 623/22.15 |
| 6,497,728 B2 | * | 12/2002 | Yong | A61F 2/30907 623/23.22 |
| 6,716,250 B2 | * | 4/2004 | Ganjianpour | A61F 2/3609 623/22.42 |

(Continued)

*Primary Examiner* — Jan Christopher Merene
*Assistant Examiner* — Steven Cotroneo (57) ABSTRACT

A hip implant has a neck body that connects to a bone fixation body. The bone fixation body has a porous structure with an elongated shape. An internal cavity is formed in the bone fixation body and includes a substance to stimulate bone growth.

17 Claims, 8 Drawing Sheets

(56) References Cited

U.S. PATENT DOCUMENTS

| | | | | |
|---|---|---|---|---|
| 7,981,161 | B2* | 7/2011 | Choi | A61F 2/36 |
| | | | | 623/22.42 |
| 8,814,567 | B2* | 8/2014 | Zhang | A61C 8/0006 |
| | | | | 433/173 |
| 2002/0151984 | A1* | 10/2002 | White | A61F 2/30734 |
| | | | | 623/23.22 |
| 2003/0074079 | A1* | 4/2003 | McTighe | A61F 2/30767 |
| | | | | 623/22.42 |
| 2004/0107001 | A1* | 6/2004 | Cheal | A61F 2/36 |
| | | | | 623/22.42 |
| 2006/0229734 | A1* | 10/2006 | Yoon | A61L 27/12 |
| | | | | 623/23.46 |
| 2010/0211120 | A1* | 8/2010 | Bonutti | A61B 17/0401 |
| | | | | 606/86 R |
| 2011/0123951 | A1* | 5/2011 | Lomicka | A61C 8/0012 |
| | | | | 433/174 |
| 2013/0030546 | A1* | 1/2013 | Bandoh | A61F 2/36 |
| | | | | 623/23.34 |

* cited by examiner

HIP IMPLANT WITH POROUS BODY

BACKGROUND OF THE INVENTION

Much effort has been directed to integrating hip implants into surrounding bone. Ideally, a hip implant would be placed into the femur, and thereafter bone would readily grow into the surface of the implant. To achieve this objective, many different surface technologies have been applied to hip implants. In some instances, the surface of the implant is roughened, grit-blasted, plasma-sprayed, or microtextured. In other instances, the surface is coated with a biological agent, such as hydroxylapatite (known as HA). In all of these instances, the goal is the same: Produce a surface on the hip implant into which surrounding bone will grow or bond.

Porous coatings have also been applied to surfaces of hip implants. Porous surfaces are often thin coatings applied to the metallic substrate of the implant. Bone surrounding the implant can only grow into the thin coating itself. Bone cannot grow through the coating and into the metallic substrate. The depth of bone growth into the implant is limited to the depth of the porous coating. Bone simply cannot grow completely through the implant or deeply into the body of the implant.

SUMMARY OF THE INVENTION

One example embodiment is a hip implant that includes a bone fixation body that connects to a neck body. The bone fixation body is formed of a porous structure that extends through a center of the bone fixation body in a cross-sectional view of the bone fixation body. An internal cavity is located in the porous structure of the bone fixation body. This internal cavity includes a substance to stimulate bone growth.

DETAILED DESCRIPTION

In one example embodiment, a hip implant includes two separate and distinct bodies, a neck body and a bone fixation body. Together, these bodies connect together to form a femoral hip implant.

The bone fixation body is formed of a porous structure, such as titanium, tantalum, or other metals, polymers, or alloys suitable for a hip prosthesis. The bone fixation body has at least one cross-section in which the porous structure is completely porous. This completely porous structure can extend through a portion of the bone fixation body (e.g., throughout a cross-section) or through the entire body of the bone fixation body. For example in one embodiment, the bone fixation body is completely porous from its proximal to distal ends and does not include a metal substrate. In another example embodiment, a portion of the bone fixation body is completely porous and does not include a metal substrate. In at least one cross-sectional view then, the bone fixation body has a porous structure with no solid metal substrate.

In one example embodiment, the porous structure extends entirely through a cross-section of the bone fixation body of the hip implant along the region where the hip implant engages femoral bone. As such, the depth of bone growth into the hip implant is not restricted to a thin porous coating. Instead, bone can grow deeply into the bone fixation body of the hip implant or completely into and even through the bone fixation body of the hip implant (i.e., bone can grow from one side of the hip implant through its center and to another oppositely disposed side). The hip implant can become fully integrated into surrounding bone with the structure of bone dispersed throughout the bone fixation body of the hip implant.

In one example embodiment, the geometric structure of the porous structure of the bone fixation body is shaped and sized to emulate the shape and size of natural bone surrounding the hip implant. The porous structure of the bone fixation body thus replicates the porous structure of natural bone itself. The porous structure readily accepts and encourages surrounding bone to grow into and even through the bone fixation body of the hip implant.

In one example embodiment, the bone fixation body includes an internal cavity with a substance that causes and/or stimulates bone growth. This internal cavity can be enclosed within the bone fixation body without an egress or ingress. Alternatively, one or more openings in the bone fixation body or hip implant can lead to the internal cavity.

In one example embodiment, the bone fixation body and/or internal cavity include one or more substances to cause and/or stimulate bone growth. This substance can be placed throughout the bone fixation body and/or internal cavity so bone grows deeply into the hip implant or completely through the hip implant from one side to an oppositely disposed side. Bone growth, as such, is not restricted to the surface of the hip implant.

In one example embodiment, the substance in the internal cavity includes a porous structure that causes and/or stimulates bone growth from within the internal cavity. Bone grows from the internal cavity toward an exterior surface of the bone fixation body. After the hip implant is implanted, bone can thus simultaneously grow from the internal cavity toward an exterior surface of the bone fixation body and from the exterior surface of the bone fixation body toward the internal cavity. New bone growth thus concurrently occurs and originates from two separate and distinct locations (i.e., from locations within the hip implant and from locations exterior to the hip implant).

As noted, the porous structure of the hip implant enables bone to grow deeply into or completely through the hip implant or portions of the hip implant. Bone growth deep into the body of the hip implant provides a strong interface between the hip implant and surrounding natural bone. As such, the likelihood that the hip implant will loosen is reduced. Further, the overall long-term acceptance of the hip implant in the bone is increased. Further yet, the porous structure of the bone fixation body and internal cavity reduce the overall weight of the hip implant. The size and shape of the internal cavity also enables the physical properties of the bone fixation body to more closely emulate the physical properties of natural bone.

Figure 1:
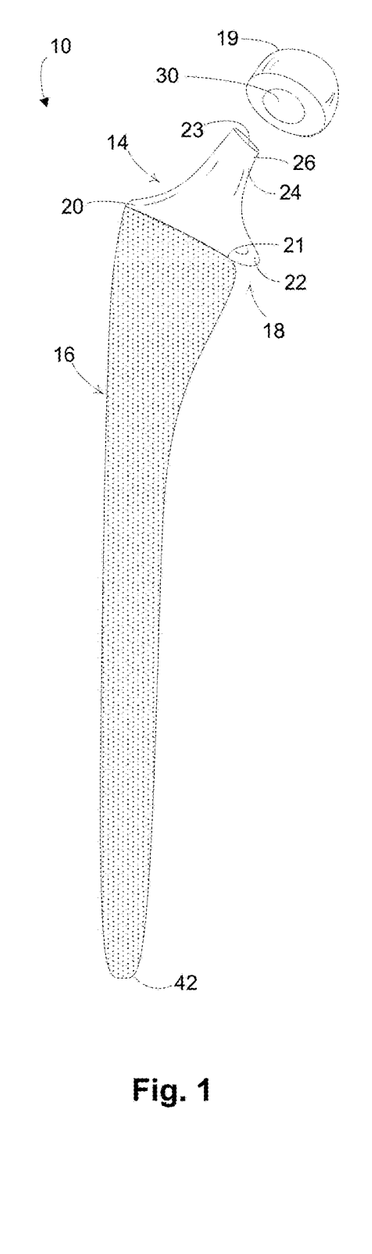
FIG. 1 is a side view of an example embodiment of a hip implant.
Figure 2:
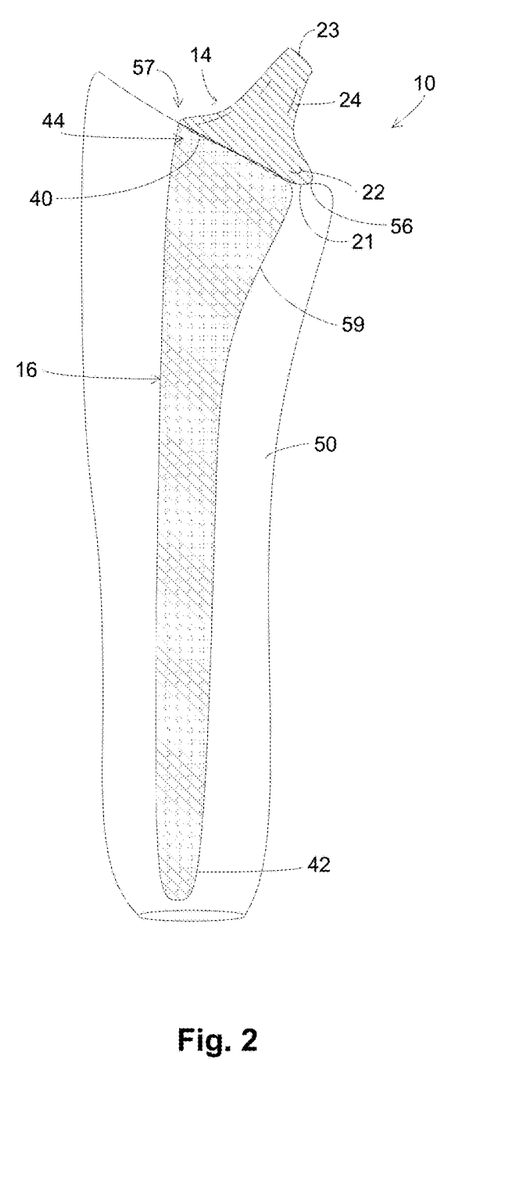
FIG. 2 is a cross-sectional view of the implant of FIG. 1 embedded in the intramedullary canal of a femur.

Referring to FIGS. 1 and 2, a hip implant 10 is shown according to an exemplary embodiment of the invention. Implant 10 is preferably constructed of a biocompatible material such as titanium, titanium alloy, or other metals or alloys suitable for a hip prosthesis. Implant 10 comprises two primary components or bodies, a neck body 14 and a bone fixation body 16.

The neck body 14 is located at the proximal end 18 of the hip implant 10 and functions to connect the hip implant 10 to a spherically shaped femoral ball 19 and acetabular component (not shown). The neck body extends from a flat or planar distal end surface 21 to a proximal end surface 23. Further, the neck body has a base portion 20 that includes a collar 22 adapted to seat against a resected or end portion of a femur. An interface is adapted to connect the neck body to the femoral ball. A neck portion 24 extends outwardly from the base portion 20. This neck portion has a short cylindrical configuration and has an end 26 with a slight taper. This end 26 is adapted to be received in a correspondingly shaped and sized cylindrical recess 30 in the femoral ball 19. Together, end 26 and recess 30 form a Morse taper connection.

Preferably, the neck body 14 is formed of a biocompatible metal, such as a solid metal piece of titanium, titanium alloy or other metals or alloys suitable for a hip prosthesis. The body can be machined to have a size and shape shown in the figures or other sizes and shapes adapted for use as a hip implant.

The bone fixation body 16 has an elongated tapering shape that extends from a flat or planar proximal end surface 40 to a rounded distal end surface 42. The distal end surface 21 of neck body 14 connects or fuses to the proximal end surface 40 of the bone fixation body 16 at a junction 44.

In the exemplary embodiments of FIGS. 1 and 2, bone fixation body 16 is formed from a porous metal, such as titanium. The body has a completely porous structure that extends throughout the entire body from the proximal end surface 40 to distal end surface 42. Specifically, as shown in FIG. 2, body 16 does not include a solid metal substrate.

FIG. 2 shows the implant 10 embedded in a femur 50 of a patient. In this embodiment, the implant is embedded into the intramedullary canal 52 of the femur. The length of the bone fixation body 16 extends along the region where the implant contacts surrounding bone. As shown, the collar 22 seats against a resected end 56 of the femur above an entrance 57 to the intramedullary canal 59. In this embodiment, the bone fixation body 16 extends into the intramedullary canal, and the neck body 14 extends outwardly from the resected end of the intramedullary canal and femur. Further, the proximal end surfaced 40 is adjacent the entrance 57 to the intramedullary canal.

As noted, the bone fixation body 16 has a porous structure that extends throughout the body from the proximal end surface to the distal end surface. By "porous," it is meant that the material at and under the surface is permeated with interconnected interstitial pores that communicate with the surface. The porous structure can be formed by sintering titanium, titanium alloy powder, metal beads, metal wire mesh, or other suitable materials, metals, or alloys known in the art.

The porous structure of body 16 is adapted for the ingrowth of cancellous and cortical bone spicules. In the exemplary embodiment, the size and shape of the porous structure emulates the size and shape of the porous structure of natural bone.

Preferably, the average pore diameter of body 16 is about 40 µm to about 800 µm with a porosity from about 45% to 65%. Further, the interconnections between pores can have a diameter larger than 50-60 microns. In short, the geometric configuration of the porous structure should encourage natural bone to migrate and grow into and throughout the entire body 16. Although specific ranges are given for pore diameters, porosity, and interconnection diameters, these ranges are exemplary and are applicable to one exemplary embodiment. In other embodiments, these ranges could be modified, and the resulting hip implant still within the scope of the invention.

Preferably, body 16 is created with a sintering process. One skilled in the art will appreciate that many variations exist for sintering, and some of these variations may be used to fabricate the present invention. In the exemplary embodiment, the neck body is formed from a solid piece of metal and prepared using conventional and known machining techniques. Next, a ceramic mold is provided. The mold has a first cavity that is sized and shaped to match the size and shape of the bone fixation body. In this first cavity, the sintering material can be placed. The mold also has a second cavity that is adjacent and connected to the first cavity. This second cavity is sized and shaped to receive the neck body. The neck body is positioned in the second cavity such that the distal end surface is adjacent and continuous with the first cavity.

The sintering material is then placed into the first cavity. This material may be a titanium alloy powder, such as Ti-6Al-4V. Some of this powder will contact the distal end surface of the neck body. The mold is then heated to perform the sintering process. During this process, as the material in the first cavity heats and sinters, the bone fixation body forms and simultaneously bonds or fuses to the distal end surface of the neck body.

The size and shape of the pores and porous structure produced in the first cavity depend on many factors. These factors include, for example, the temperature obtained in the furnace, the sintering time, the size and shape of sintering material, the composition of the sintering material, and the type of ceramic mold used. These factors (and others) can be varied to produce a bone fixation body in accordance with the present invention. Further, these factors (and others) can be varied to produce a strong bond between the bone fixation body and neck body.

Once the sintering process is finished, the neck body is directly fused to the bone fixation body. These two bodies are now permanently connected together to form the hip implant.

In the aforementioned sintering process, the bone fixation body simultaneously forms and attaches to the neck body. One skilled in the art though will appreciate that each of these bodies can be fabricated independently and subsequently connected together. If the bodies are made separately, then they may be attached or fused together using known welding or brazing techniques, for example.

In FIG. 1, for example, the bone fixation body has an elongated tapering body with a slight bow. The bone fixation body, though, may have other configurations and still be within the scope of the invention. The size and shape of the body depend on the size and shape of the cavity of the mold during the sintering process. This cavity can be shaped, for example, to emulate the natural size, shape, and contour of a human intramedullary canal. As such, the bone fixation body will more naturally fit into the intramedullary canal and conform to the natural anatomical contours of a human patient.

Figure 3:
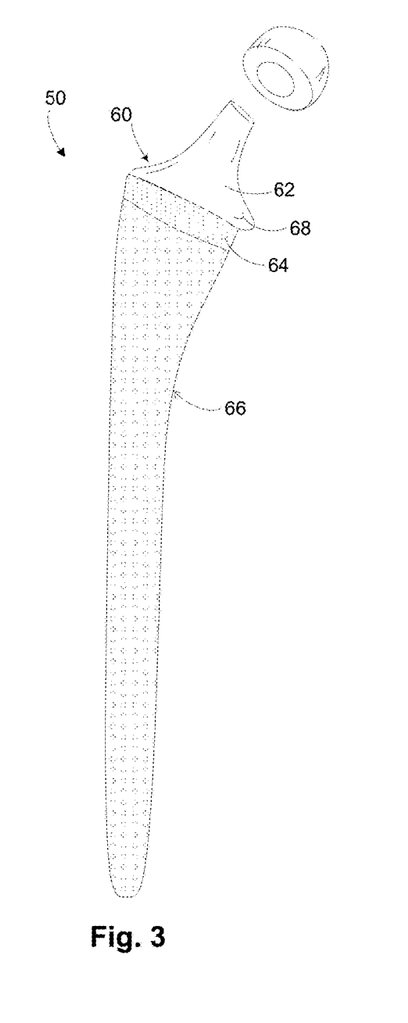
FIG. 3 is a side view of another example embodiment of a hip implant.
Figure 4:
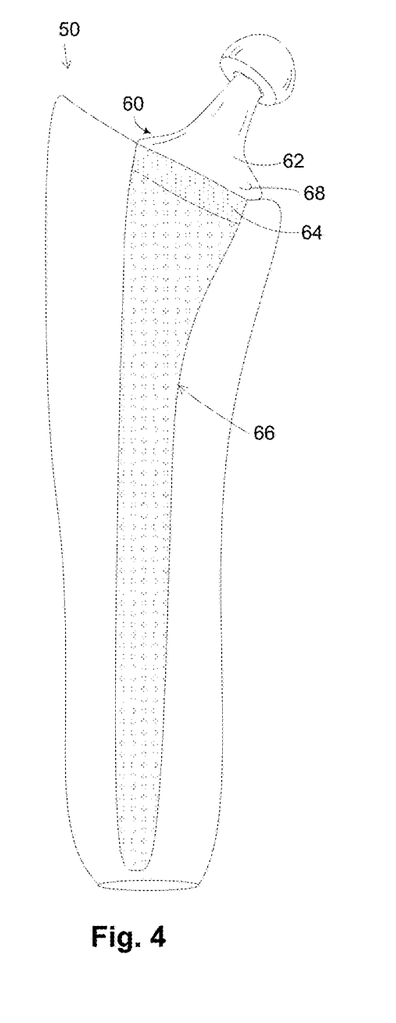
FIG. 4 is a cross-sectional view of FIG. 3 showing the hip implant embedded in the intramedullary canal of a femur.

FIGS. 3 and 4 show another hip implant 50 according to an exemplary embodiment of the invention. With some differences, implant 50 is similarly configured to the implant 10. As one difference, the neck body 60 of implant 50 has two different and distinct regions on its outer surface. A first region 62 has a smooth outer surface. A second region 64 has a bone-engaging surface that is contiguous and adjacent to the first region 62 on one side and contiguous and adjacent the porous bone fixation body 66 on the other side. The second region is non-porous and is shaped as a band that extends completely around the neck body. This second region can be formed on the outer surface of the neck body with various techniques. These techniques include, for example, coating with HA, grit-blasting, etching, micro-texturing, other non-porous surface treatments, or combinations of these techniques. This surface 64 is provided as an intermediate zone between the porous body and the smooth first region 62.

As shown in FIG. 4, the second region 64 is below collar 68 and is positioned into the intramedullary canal to contact bone. Region 64, then, contacts bone, and region 62 does not contact bone and extends above it.

Figure 5:
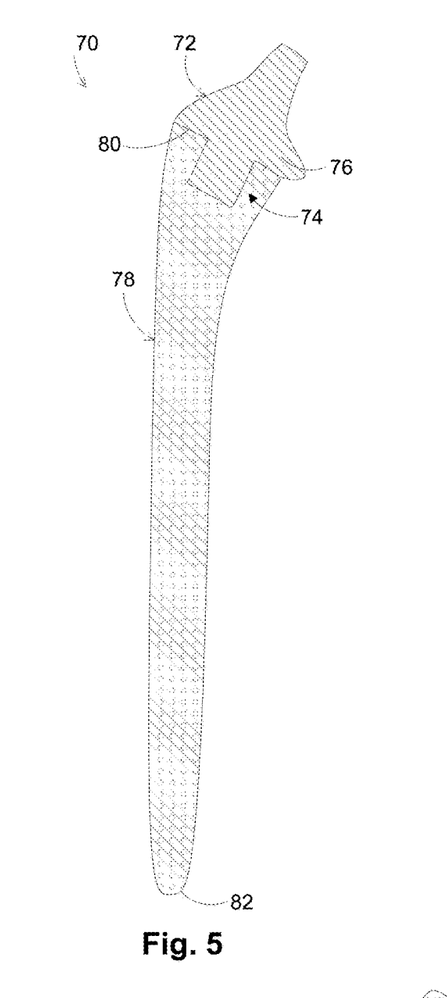
FIG. 5 is a side cross-sectional view of yet another example embodiment of a hip implant.

FIG. 5 shows another implant 70 according to another exemplary embodiment of the invention. With some differences, implant 70 is similarly configured to the implant 10. As one difference, neck body 72 includes a male protrusion 74 that extends outward from base portion 76. This protrusion 74 is adapted to extend partially into the bone fixation body 78 of implant 70. The protrusion 74 forms a core for the bone fixation body. As shown in FIG. 5, this protrusion extends past the proximal end surface 80 and into the bone fixation body. The depth of the protrusion into the bone fixation body can be increased or decreased in various embodiments and still remain within the scope of the invention. For example, the protrusion can partially extend into the bone fixation body and remain substantially near the proximal end surface. Alternatively, the protrusion can extend farther into the bone fixation body toward the distal end surface 82. In this latter embodiment, the protrusion gradually tapers as it extends toward the distal end surface.

The size and shape of the protrusion can also have various embodiments and still remain within the scope of the invention. For example, the protrusion can be cylindrical or polygonal, such as rectangular or square. Other configurations are possible as well; the protrusion can taper or have longitudinal ribs placed along its outer surface. The size and shape of the protrusion can have various embodiments to serve various functions. For example, the protrusion can be sized and shaped to provide a strong connection between the neck body and bone fixation body. The protrusion can be sized and shaped to provide an anti-rotational interface between the neck body and bone fixation body. Further, the protrusion can be sized and shaped to provide additional strength to the bone fixation body or more equally or efficiently distribute loads from the neck body to the bone fixation body. Other factors as well may contribute to the design of the protrusion.

Figure 6:
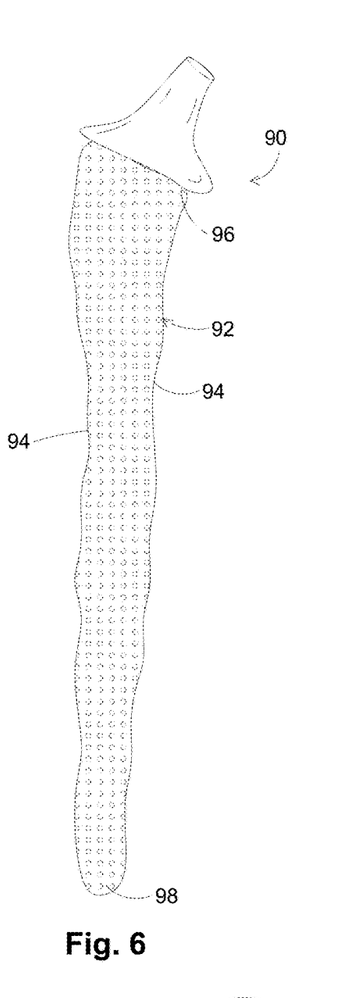
FIG. 6 is a side view of yet another example embodiment a hip implant.

FIG. 6 shows another implant 90 according to an exemplary embodiment of the invention. Implant 90 has a bone fixation body 92 with an outer surface that has a plurality of undulations 94, such as hills and valleys. These undulations may be provided as tiny ripples or waves. Alternatively, the undulations may be larger and more rolling. Regardless, the undulations are adapted to firmly secure the implant into the intramedullary canal of the femur after the implant is placed therein.

As shown in FIG. 6, the undulations extend along the entire length of the bone fixation body 92 from the proximal end surface 96 to the distal end surface 98. In alternative embodiments, the undulations do not extend along the entire length of the bone fixation body, but partially extend along this body.

Figure 7:
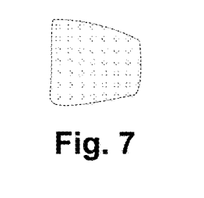
FIG. 7 is a top view of a horizontal cross section of an example embodiment.
Figure 8:
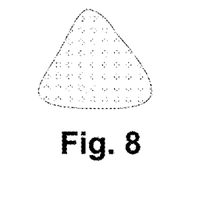
FIG. 8 is a top view of a horizontal cross section of another example embodiment.
Figure 9:
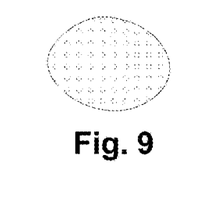
FIG. 9 is a top view of a horizontal cross section of yet another example embodiment.

FIGS. 7-9 show various longitudinal cross-sectional shapes of the bone fixation body for different exemplary embodiments of the invention. The bone fixation body may have one single longitudinal cross-sectional shape, or the body may have numerous different longitudinal cross-sectional shapes. FIGS. 7-9 represent examples of some of these shapes.

FIG. 7 shows a trapezoidal longitudinal cross-sectional shape. FIG. 8 shows a triangular longitudinal cross-sectional shape. FIG. 9 shows an elliptical or oval longitudinal cross-sectional shape.

The bone fixation body can be adapted to induce bone growth partially into or entirely through the body. The body, for example, can be doped with biologically active substances. These substances may contain pharmaceutical agents to stimulate bone growth all at once or in a timed-release manner. Such biological active substances are known in the art.

Figure 10A:
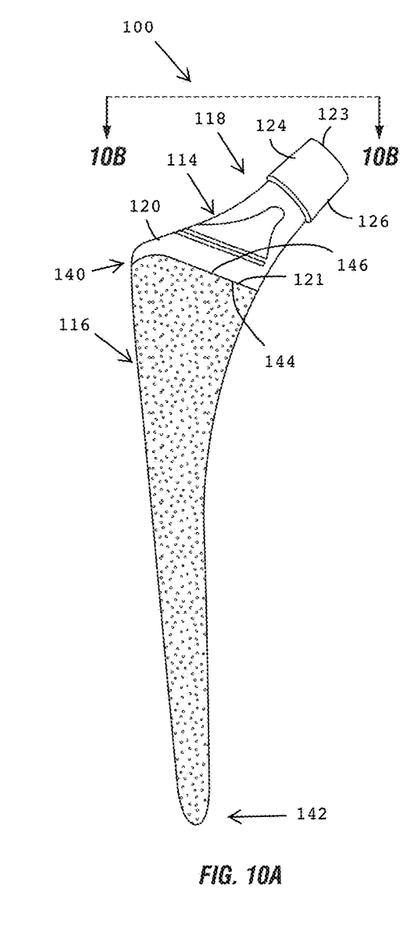
FIG. 10A is another example of a hip implant.
Figure 10B:
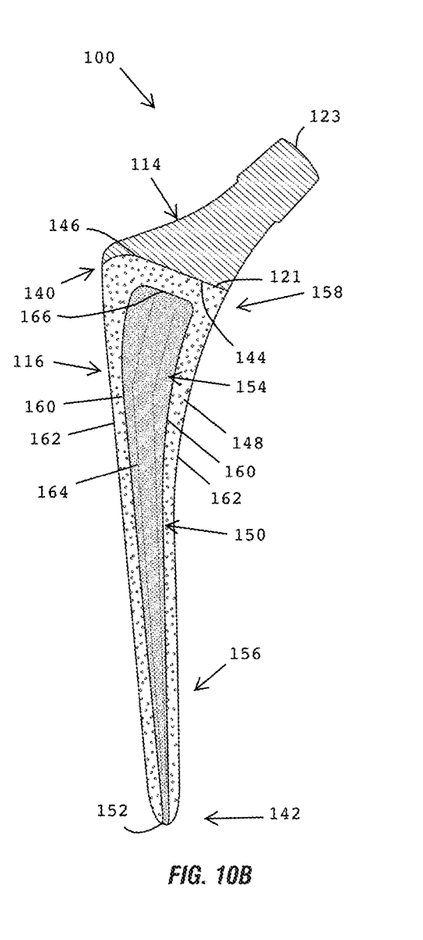
FIG. 10B is a cross-section taken along lines 10B-10B of the hip implant in FIG. 10A.

FIGS. 10A and 10B show a hip implant 100 according to an example embodiment. The hip implant 100 comprises two primary components or bodies, a neck body 114 and a bone fixation body 116.

The neck body 114 is located at the proximal end 118 of the hip implant 100 and functions to connect the hip implant 100 to a spherically shaped femoral ball and acetabular component. The neck body extends from one or more flat or planar distal end surfaces 121 to a proximal end surface 123. A neck portion 124 extends outwardly from a base portion 120. This neck portion has a short cylindrical configuration and has an end 126 with a slight taper. This end 126 is adapted to be received in a correspondingly shaped and sized cylindrical recess in the femoral ball (shown in FIGS. 1 and 2).

Preferably, the neck body 114 is formed of a biocompatible metal, such as one or more of a solid metal piece of titanium, titanium alloy, polymer, or other metals or alloys suitable for a hip prosthesis. The neck body can be machined, casted, molded, or otherwise configured to have a size and shape shown in the figures or other sizes and shapes adapted for use as a hip implant.

The bone fixation body 116 has an elongated tapering shape that extends from a proximal end 140 to a rounded distal end 142. The proximal end includes one or more flat or planar surfaces 144. One or more of these surfaces connect to the distal end surfaces 121 of the neck body 114 at an interface or junction 146.

As shown in FIG. 10B, the bone fixation body 116 forms a shell 148 with a completely porous structure that extends throughout the entire bone fixation body from the proximal end 140 to the distal end 142. This shell 148 has a hollow center that forms an internal chamber or cavity 150 located inside the bone fixation body 116. The internal cavity 150 extends from a location adjacent the interface 146 to the distal end 142. A circular opening 152 leads into the internal cavity 150 and forms at the distal end 142 of the bone fixation body 116. The internal cavity 150 is thus enclosed inside of the porous structure of the bone fixation body 116.

As shown in FIG. 10B, the internal cavity 150 includes a substance 154 to cause or stimulate bone growth. This substance 154 fills the internal cavity 150 from a proximal end surface of the internal cavity to an oppositely disposed distal end surface of the internal cavity. Alternatively, the substance can partially fill the internal cavity or be absent from the internal cavity.

A shape and/or size of the internal cavity 150 can vary along its longitudinal length. In an example embodiment, this shape matches or emulates the external shape of the bone fixation body 116. As the size and/or shape of the bone fixation body 116 changes, the size and/or shape of the internal cavity 150 correspondingly changes. With regard to size for example, as the cross-sectional diameter of the bone fixation body increases or decreases, the cross-sectional diameter of the internal cavity proportionally increases or decreases to match the increases or decreases in the diameter of the bone fixation body. With regard to shape for example, the bone fixation body 116 has an elongated cylindrical or elliptical shape at a distal end portion 156 in cross-section. Likewise, the internal cavity 150 has an elongated cylindrical or elliptical shape at this distal end portion 156. At a proximal end portion 158, the bone fixation body has a rectangular or trapezoidal shape in cross-section. Likewise, the internal cavity 150 has a rectangular or trapezoidal shape at this proximal end portion 158. Thus, as the size and/or shape of the bone fixation body changes along its longitudinal length, the size and/or shape of the internal cavity can also change to match with or correspond to these changes.

In an example embodiment, the internal cavity 150 is centrally located inside of the bone fixation body 116 such that the sides or walls 160 of the internal cavity are equally spaced from an external surface 162 of the bone fixation body. The walls 160 can include one or more grooves 164 formed in the porous structure of the bone fixation body. These grooves form one or more channels that extend from the circular opening 152 to an end surface 166 of the internal cavity 150.

As shown in FIG. 10B, the internal cavity 150 has a larger diameter in cross-section adjacent the interface 146 at the proximal end 158 than at the distal end 156. The size of the internal cavity narrows and tapers as it transitions from the proximal end of the hip implant toward the distal end of the hip implant.

While the hip implant 100 is being positioned into the femur of the patient, bone, tissue, and/or blood enters and fills the internal cavity 150. As the hip implant passes into the medullary canal of the femur, bone, tissue, and/or blood are forced into the internal cavity and travel upwardly along the grooves 164 toward the end surface 166. The grooves guide and facilitate the passage of bone, tissue, and/or blood into the internal cavity. For example, bone travels in the grooves 164 from the opening 152 to the end surface 166 in order to fill or collect within the internal cavity 150.

The grooves 164 can be straight and extend parallel to each other from the opening 152 to the end surface 166. Alternatively, the grooves can be nonlinear, such as being curved or spiraling. Grooves facilitate the transfer of bone, tissue, and/or blood into the internal cavity 150 while the hip implant 100 is being forced, pressed, or inserted into the femur. Alternatively, the internal cavity 150 can be formed without grooves.

Figure 11A:
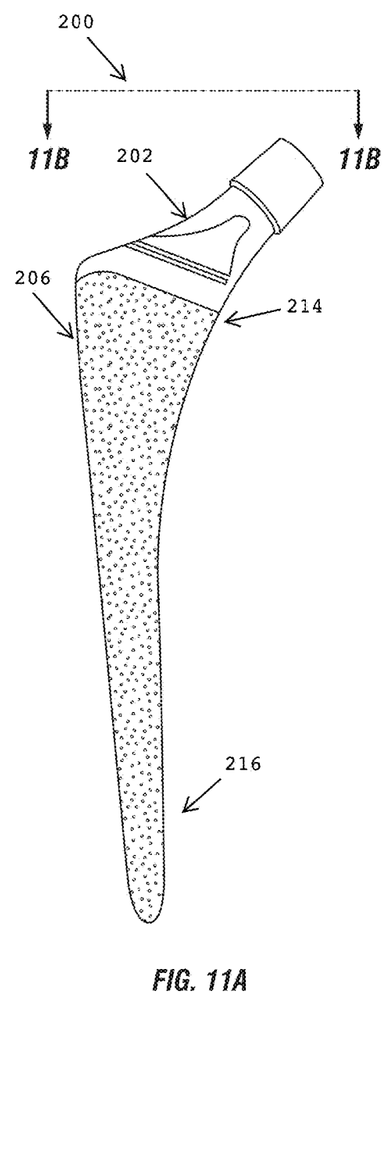
FIG. 11A is another example of a hip implant.
Figure 11B:
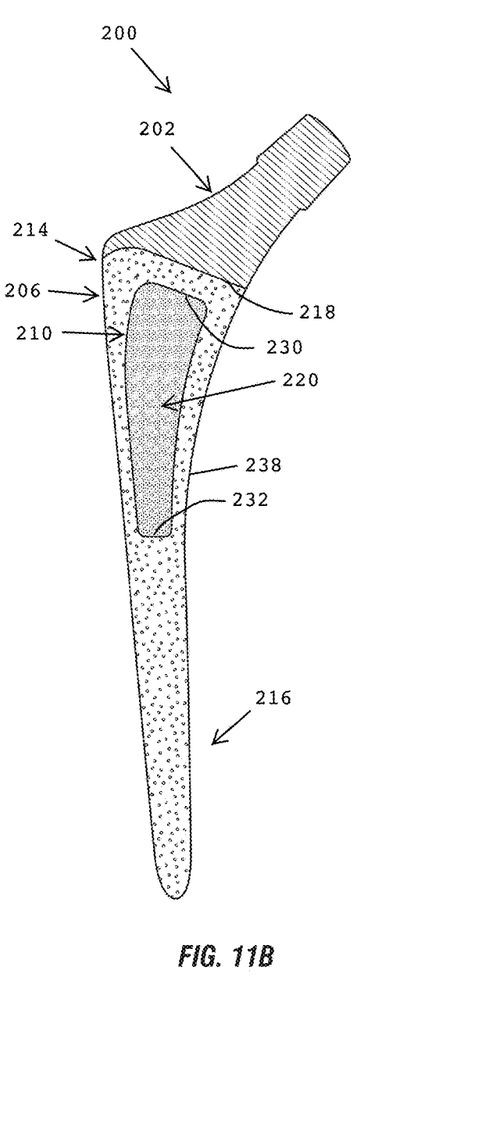
FIG. 11B is a cross-section taken along lines 11B-11B of the hip implant in FIG. 11A.

FIGS. 11A and 11B show a hip implant 200 with a neck body 202 that connects to a bone fixation body 206 according to an example embodiment. With some differences, the hip implant 200 is similarly configured to the hip implant 100 in FIGS. 10A and 10B. As one difference, the hip implant 200 includes an internal cavity 210 that is enclosed and trapped within the bone fixation body 206. One of end this internal cavity 210 is located near or adjacent a junction 218 where the neck body 202 connects to a proximal end 214 of the bone fixation body 206. Another end of this internal cavity 210 extends toward a distal end 216 of the bone fixation body 206.

In an example embodiment, the internal cavity 210 is completely enclosed within the bone fixation body 206. The bone fixation body 206 completely surrounds the sides, the top, and the bottom of the internal cavity 210 (i.e., the internal cavity is surrounded on all sides by the porous structure). As such, the internal cavity 210 lacks an ingress (such as a hole or a passageway) for entering the cavity or an egress for exiting the cavity (such as a hole or a passageway). Nonetheless, the open-celled configuration of the porous structure of the bone fixation body does allow bone to grow into and through the bone fixation body. Thus, the internal cavity can still communicate with the porous structure of the bone fixation body and with bone external to the bone fixation body through the interconnected interstitial pores to enable bone growth since the internal cavity is surrounded by and formed within an open-celled porous structure. Alternatively, the bone fixation body 206 includes openings, holes, and/or passageways from an external surface 238 to the internal cavity 210.

As shown in FIG. 11B, the internal cavity 210 includes a substance 220 to cause or stimulate bone growth. This substance 220 fills the internal cavity 210 from a proximal end surface 230 of the internal cavity to an oppositely disposed distal end surface 232 of the internal cavity. Alternatively, the substance can partially fill the internal cavity or be absent from the internal cavity.

In one example embodiment, the substance 220 is trapped within the enclosed internal cavity. For example, the substance is placed in the internal cavity during manufacturing or formation of the hip implant. Alternatively, the substance is placed in the internal cavity after the hip implant is constructed. For instance, a small opening is formed through the hip implant, the substance is placed through the opening and into the internal cavity, and then the opening is sealed and/or closed. As yet another example, the substance is liquefied and forced through the interconnected interstitial pores of the bone fixation body and into the internal cavity. In this example, the substance travels from the exterior surface 238, through the bone fixation body 206, and into the internal cavity 210.

In an example embodiment, the substance in the internal cavity and/or porous structure of the bone fixation body activates and/or grows bone when bone, tissue, and/or blood enter into the internal cavity. For example, one or more blood vessels, arteries, and canals supply blood to the substance.

Figure 12:
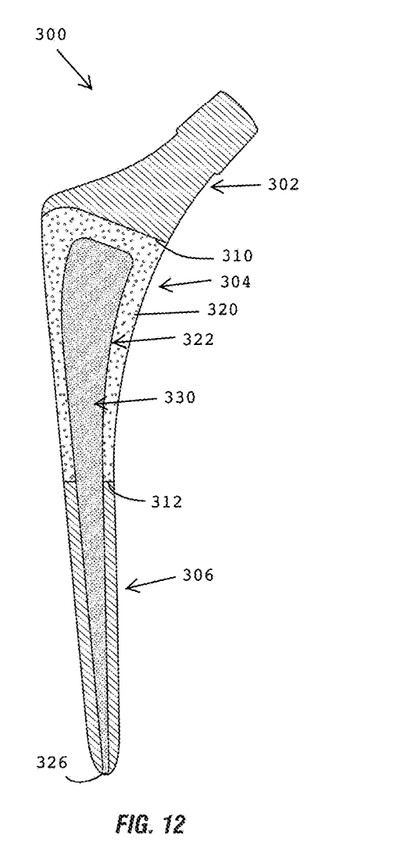
FIG. 12 is a cross-section of another example of a hip implant.

FIG. 12 shows a cross-sectional view of another hip implant 300 according to an example embodiment. The hip implant 300 includes a neck body 302, a bone fixation body 304, and a distal body 306. The neck body 302 connects to the bone fixation body 304 at a junction 310, and the bone fixation body 304 connects to the distal body 306 at a junction 312.

The bone fixation body 304 includes a porous structure 320 that surrounds an internal cavity 322. This internal cavity extends from a location adjacent the junction 310 to an opening 326 at the distal end of the distal body 306. A substance 330 to cause and/or stimulate bone growth is located inside of the internal cavity of the bone fixation body and the distal body.

Internal cavity 322 extends through a center of the distal body 306 along a longitudinal central axis of the distal body. Bone, tissue, and/or blood travel through the opening 326, through the internal cavity of the distal body 306, and into the internal cavity at the proximal end of the bone fixation body 304. For example, bone, tissue, and/or blood enter the internal cavity of the bone fixation body and distal body while the hip implant is being implanted into the femur of the patient.

In an example embodiment, the internal cavity of the bone fixation body and distal body are in fluid communication with each other such that the substance 330 or another substance (such as bone, tissue, and/or blood) located inside these cavities can flow or migrate between the bone fixation body and the distal body. As discussed herein, the substance, however, is not limited to being a fluid, but can be a solid structure, such as a scaffold, a membrane, a powder, a metal, a polymer, and/or other biocompatible materials.

Figure 13:
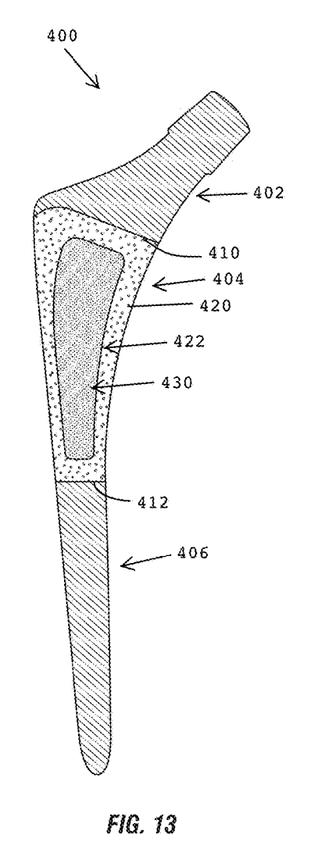
FIG. 13 is a cross-section of another example of a hip implant.

FIG. 13 shows a cross-sectional view of another hip implant 400 according to an example embodiment. The hip implant 400 includes a neck body 402, a bone fixation body 404, and a distal body 406. The neck body 402 connects to the bone fixation body 404 at a junction 410, and the bone fixation body 404 connects to the distal body 406 at a junction 412.

The bone fixation body 404 includes a porous structure 420 that surrounds an internal cavity 422. This internal cavity extends from a location adjacent the junction 410 to a location adjacent the junction 412. A substance 430 to cause and/or stimulate bone growth is located inside of the internal cavity 422 of the bone fixation body 404.

In FIGS. 12 and 13, the neck body thus forms a proximal section of the hip implant; the bone fixation body forms a middle section of the hip implant; and the distal body forms a distal section of the hip implant. Additionally, the bone fixation body is formed of a porous structure, while the neck body and the distal body include a non-porous structure, such as having a substrate or base formed of solid metal, metal alloy, polymer, and/or other biocompatible material. For example, the neck body and distal body are formed of solid metal with a porous structure, microtexture, or bone stimulating substance on their outer surfaces. The non-porous structure of the neck body and the distal body can be the same, similar, or different from each other. As one example, the neck body and the distal body include a non-porous substrate formed of solid metal, while the bone fixation body is formed of a porous substrate. As another example, the neck body is formed having a first material (such as a solid substrate or underlying layer formed of one metal); the bone fixation body is formed having a second material different than the first material (such as a porous structure); and the distal body is formed having a third material different than the first and second materials (such as solid substrate or underlying layer formed of another metal or a porous structure formed to include a different material than the porous structure of the bone fixation body).

In FIG. 13, the neck body 402 and the distal body 406 are structurally stronger than the bone fixation body 404 since they include a non-porous structure whereas the bone fixation body is formed to have a porous structure. As such, the bone fixation body is configured so that bone can grow completely through the porous structure. By contrast, the neck body and the distal body are configured so that bone can grow into an outer surface but not into and through center of the bodies since these locations have cores or centers filled with solid metal. For example, the outer surfaces of the neck and distal bodies are microtextured or covered with a porous structure. These surfaces can integrate with surrounding bone after the hip implant is implanted in the femur.

FIGS. 10B, 11B, 12, and 13 show the hip implant with an internal cavity. The size and shape of this internal cavity can vary depending on, for example, the size and shape of the hip implant, the substance included in the internal cavity, the mechanical properties desired for the implant, and the material used to fabricate the porous structure. By way of example, these shapes of the internal cavity include, but are not limited to, cylinders (such as right circular cylinders having a cross-section as a circle, elliptic cylinders having a cross-section as an ellipse, hyperbolic cylinders having a cross-section as a hyperbola, parabolic cylinders having a cross-section as a parabola, oblique cylinders having top and bottom surfaces displaced from each other, and tapered cylinders), cones (such as right cones, oblique cones, truncated cones, and elliptical cones), wheels (such as a shape having a cylindrical core with passageways extending off from this core), spheres, cuboids, polyhedrons, polytopes, pyramids, linear and nonlinear tunnels and pathways, symmetric and asymmetric voids and cavities, three dimensional shapes (such as shapes having curved lines, straight lines, closed configurations, and/or open configurations), and combinations of these shapes.

Additionally, the size and shape of the internal cavity can be adjusted to provide a closer biomechanical match of strength, stiffness, and architectural structure between the hip implant and the surrounding bone. The combination of pores in the porous structure and space of the internal cavity reduces the overall stiffness values of the hip implant so it can more closely resemble the stiffness values and properties of natural bone.

FIGS. 14A-14E show example horizontal cross-sections of hip implants with differently shaped internal cavities. These cross-sections show examples of hip implants in accordance with example embodiments.

Figure 14A:
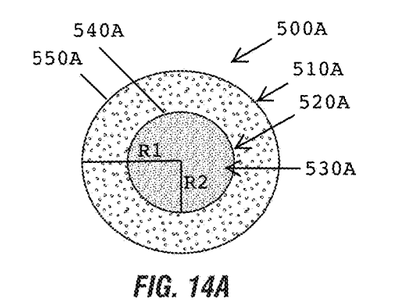
FIG. 14A is an example of a cross-section of a bone fixation body of a hip implant.

FIG. 14A is an example of a cross-section of a hip implant 500A having a bone fixation body 510A with an internal cavity 520A that is filled with a substance 530A to cause and/or stimulate bone growth. The bone fixation body 510A and the internal cavity 520A have a circular shape. An outer wall 540A that forms the exterior circumferential wall of the internal cavity is equally spaced from an outer wall 550A that forms the exterior circumferential wall of the bone fixation body.

Figure 14B:
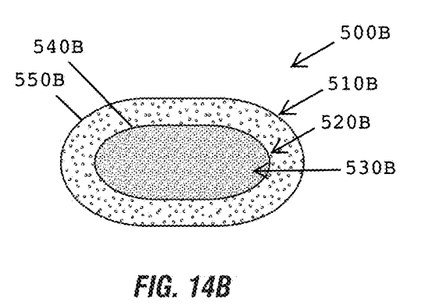
FIG. 14B is another example of a cross-section of a bone fixation body of a hip implant.

FIG. 14B is an example of a cross-section of a hip implant 500B having a bone fixation body 510B with an internal cavity 520B that is filled with a substance 530B to cause and/or stimulate bone growth. The bone fixation body 510B and the internal cavity 520B have an elliptical shape. An outer wall 540B that forms the exterior circumferential wall of the internal cavity is equally spaced from an outer wall 550B that forms the exterior circumferential wall of the bone fixation body.

Figure 14C:
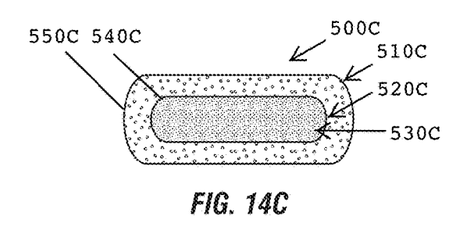
FIG. 14C is another example of a cross-section of a bone fixation body of a hip implant.

FIG. 14C is an example of a cross-section of a hip implant 500C having a bone fixation body 510C with an internal cavity 520C that is filled with a substance 530C to cause and/or stimulate bone growth. The bone fixation body 510C and the internal cavity 520C have a rectangular shape with rounded ends. An outer wall 540C that forms the exterior circumferential wall of the internal cavity is equally spaced from an outer wall 550C that forms the exterior circumferential wall of the bone fixation body.

Figure 14D:
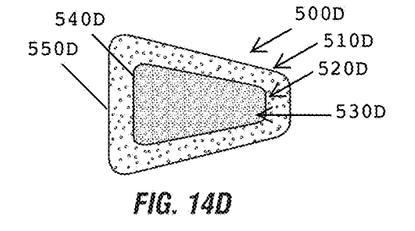
FIG. 14D is another example of a cross-section of a bone fixation body of a hip implant.

FIG. 14D is an example of a cross-section of a hip implant 500D having a bone fixation body 510D with an internal cavity 520D that is filled with a substance 530D to cause and/or stimulate bone growth. The bone fixation body 510D and the internal cavity 520D have a trapezoidal shape. An outer wall 540D that forms the exterior circumferential wall of the internal cavity is equally spaced from an outer wall 550D that forms the exterior circumferential wall of the bone fixation body.

FIGS. 14A-14D show that the shape of the internal cavity and the shape of the corresponding bone fixation body are similar. These shapes, however, can be different such as shown in FIG. 14E.

Figure 14E:
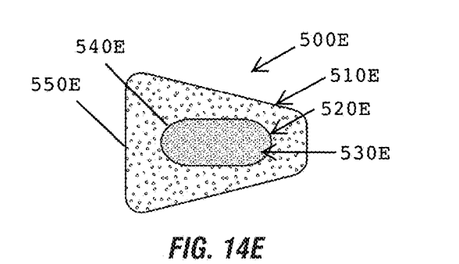
FIG. 14E is another example of a cross-section of a bone fixation body of a hip implant.

FIG. 14E is an example of a cross-section of a hip implant 500E having a bone fixation body 510E with an internal cavity 520E that is filled with a substance 530E to cause and/or stimulate bone growth. The bone fixation body 510E has a trapezoidal shape, and the internal cavity 520E has an elliptical shape. A distance varies between the outer wall 540E that forms the exterior circumferential wall of the internal cavity and an outer wall 550E that forms the exterior circumferential wall of the bone fixation body.

A size of the internal cavity with respect to the hip implant can vary. This size can change by adjusting the volume that the internal cavity occupies within the bone fixation body. By way of example, FIG. 14A shows that the bone fixation body 510A has circular shape with a radius R1, while the internal cavity has a circular shape with a radius R2. An area occupied by the bone fixation body is: $A1=\pi(R1)^2-\pi(R2)^2$, and an area occupied by the internal cavity is: $A2=\pi(R2)^2$. A percentage of area occupied by the internal cavity with respect to the bone fixation body in a cross-sectional view is: $PA=(A2/A1)\times 100$. This percentage of area occupied by the internal cavity (PA) can have values that range from about 10%-90% (such as having example values of about 10%, 15%, 20%, 25%, 30%, 35%, 40%, 45%, 50%, 55%, 60%, 65%, 79%, 75%, 80%, 85%, or 90%). As another example, this percentage of area occupied by the internal cavity (PA) has a range of about 30%-70%.

FIGS. 1-6, 10A, 10B, 11B, 11B, 12, and 13 show that the porous structure of the bone fixation body connects to the neck body at an interface or a junction. The particular cross-sectional shape of this junction where the two bodies connect depends on the shape of the bone fixation and neck bodies. For example, if the bone fixation body and the neck body are both formed as right cylinders at the junction of their interface, the junction (when viewed in a cross-section) is circular. Such a junction includes the entire volume of this circular cross-section since the circular cross-section of the bone fixation body abuts the circular cross-section of the neck body. This abutment of two circular cross-sections (or other shaped cross-sections) provides strength to the implant at the junction where the non-porous structure of the neck body connects to the porous structure of the bone fixation body.

Figure 15A:
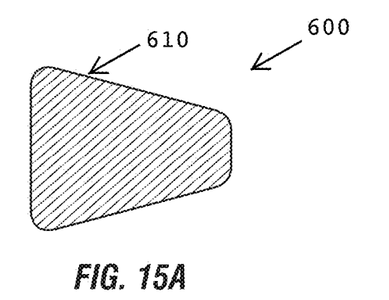
FIG. 15A is an example cross-section of a neck body of a hip implant.
Figure 15B:
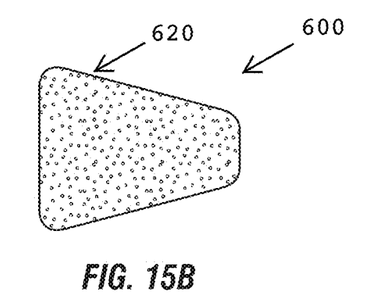
FIG. 15B is an example cross-section of a bone fixation body of a hip implant.

By way of example, FIGS. 15A and 15B show cross-sections of an example junction. FIG. 15A is an example of a hip implant 600 showing a cross-section of its neck body 610 at the junction where the bone fixation body connects to the neck body. The neck body 610 has a trapezoidal shape and is formed to have a non-porous substrate, such as being formed of solid metal. FIG. 15B is an example of the hip implant 600 showing a cross-section of its bone fixation body 620 at the junction. The bone fixation body 620 has a trapezoidal shape and is formed to have a porous structure as the substrate. A size and shape of the bone fixation body match a size and shape of the neck body at the junction.

Example embodiments include a bone fixation body with a porous structure that connects to a neck body with a non-porous structure. The structure of the neck body can be stronger than the structure of the bone fixation body. For example, the neck body is formed of a non-porous structure to provide strength to the hip implant and structural support for the porous structured bone fixation body. This added strength is useful since forces transfer to the hip implant at the neck body. Alternatively, the neck body can be formed of a porous structure, but this porous structure should be strong enough to endure the forces encountered at the proximal end of the hip implant.

Figure 16:
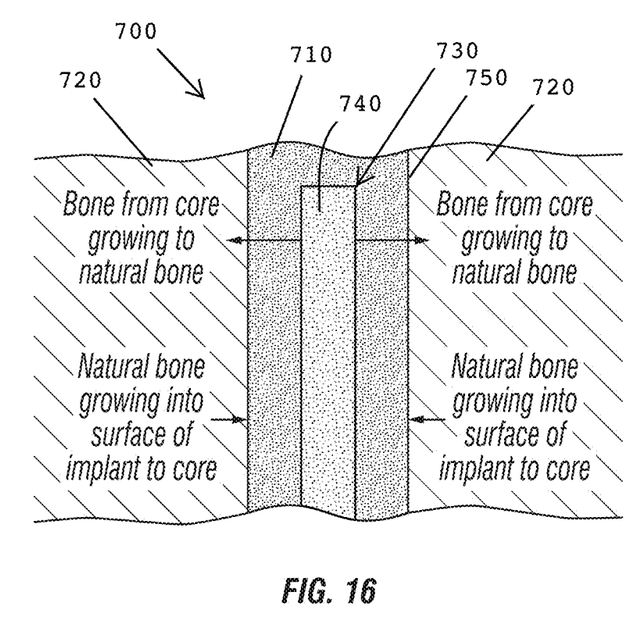
FIG. 16 is a partial cross-sectional view of a hip implant embedded in a femur of a patient.

FIG. 16 is a partial cross-sectional view of a hip implant embedded in a femur of a patient. For example, this cross-section can represent the proximal end of the bone fixation body of the hip implant shown in FIGS. 10B, 11B, 12, and 13.

As shown in FIG. 16, the hip implant 700 includes a bone fixation body 710 that is embedded in a femur bone 720 of a patient. This bone includes cortical bone and/or cancellous bone. The bone fixation body 710 includes an internal cavity 730 that is filled with a substance 740 to cause and/or stimulate bone growth.

Once the hip implant 700 is implanted into the femur bone 720, bone simultaneously begins to grow with natural bone growing inwardly toward the internal cavity 730 and bone from the substance growing outwardly from the internal cavity 730 toward the natural bone 720 that is growing inwardly. Natural bone 720 surrounding the hip implant 700 begins to grow into the outer surface 750 of the bone fixation body 710. At the same time, bone begins to grow outwardly from the internal cavity 730 and toward the outer surface 750. The substance causes and/or stimulates bone to grow outwardly from the internal cavity.

The porous structure of the bone fixation body thus supports bone growth inwardly towards the center of the hip implant and outwardly away from the center of the hip implant. Thus, bone grows from two different and separately located sources (one source being the natural bone located outside of the hip implant and a second source being the substance 740 located inside of the hip implant). This process of concurrently growing bone from two different locations (i.e., from within the hip implant and from outside of the hip implant) decreases the time required for bone to grow throughout the hip implant including the center of the hip implant where the substance is located. For example, the time required for bone to grow from one side of the bone fixation body to an oppositely disposed side of the bone fixation body is reduced since bone is concurrently growing both toward the center of the bone fixation body and outwardly from this center immediately after the hip implant is implanted into the femur. This process also decreases the time required for bone to completely fill the porous structure of the bone fixation body since bone grows in multiple different directions. For instance, bone simultaneously grows in directions from the internal cavity through sides of the cavity, through the top of the cavity, and through the bottom of the cavity. Additionally, bone grows through the sides and the bottom of the exterior surfaces of the bone fixation body. The hip implant is thus able to more quickly fully integrate with bone after being implanted (for example, more quickly have bone grow throughout the entire structure of the bone fixation body). Growing bone from the center of the hip implant thus expedites the time required to complete the bone integration process.

In an example embodiment, the porous structure of the bone fixation body is different than the structure of the substance located in the internal cavity in the bone fixation body. The geometry and material composition of the porous structure of the bone fixation body and the substance in the internal cavity both induce bone formation throughout the internal cavity and the bone fixation body. The geometry and material composition of the porous structure of the bone fixation body, however, also provides strength to the hip implant since it bears loads from forces on the hip implant (for example, forces generated while the patient is standing and/or moving). A majority of these loads pass along the bone fixation body and not to the substance located in the internal cavity. As such, the geometry and material composition of the substance can be for stimulating bone growth, whereas the geometry and material composition of the bone fixation body can be for stimulating bone growth and for providing strength to the hip implant.

In an example embodiment, the substance includes a porous structured scaffold that is inserted or fabricated in the internal cavity of the bone fixation body. This scaffold has a geometry and material composition to induce bone growth through the internal cavity and into the surrounding walls of the bone fixation body. In one example embodiment, this scaffold would not have to support equivalent loads supported by the exterior of the bone fixation body surrounding the internal cavity. Alternatively, the geometry and material composition of the substance located in the internal cavity can also be for supporting loads and providing strength to the hip implant.

In an example embodiment, the substance in the internal cavity is activated when the hip implant is placed into the femur of the patient. As one example, looking to FIGS. 10B and 12, the substance is located in the internal cavity. While the hip implant is being placed into the femur, bone, tissue, blood, and other substances pass through the opening at the distal end, come in contact with the substance in the internal cavity, and activate this substance to begin stimulating bone growth in the internal cavity. As another example, looking to FIGS. 11B and 13, while the hip implant is being placed into the femur, a fluid (including one or more of bone, tissue, blood, and other substances created from the implantation procedure) seeps or passes through the porous structure of the bone fixation body and comes in contact with the substance in the internal cavity. This fluid activates this substance to begin stimulating bone growth in the internal cavity. Alternatively, bone growth and bone stimulation properties of the substance are activated with an agent (for example, an external agent applied to the structure and/or the substance during implantation). As yet another example, passageways or holes are placed in the bone fixation body. These passageways allow bone, tissue, blood, and other substances to enter the internal cavity and cause, assist, and/or activate bone growth. As another example, the substance in the internal cavity activates after the hip implant is implanted and blood is supplied to the substance.

The substance to cause or stimulate bone growth can be formed from a variety of different materials and different processes. As one example, the substance includes a mixture of one or more bone morphogenetic proteins (BMPs) and one or more carriers. For instance, this mixture includes BMP 4, collagen, and a polymer, such as poly (lactic-co-glycolic acid) (PLGA) or poly (L-lactide) (PLLA). As another example, the substance includes one or more of natural bone and/or tissue and/or blood from the patient receiving the implant, tantalum, an acrylate based polymer, biphasic calcium phosphate (BCP), carboxymethylcellulose (CMC), hydroxypropylmethylcellulose (HPMC), hydroxyapatite (HA), tricalcium phosphate (TCP), stem cells (including human embryonic stem cells and adult stem cells), bone marrow-derived stromal cells, human bone-derived cells (hPBDs), biodegradable polymers (such as poly (glycolic acid) (PGA) and poly (lactic acid) (PLA)), poly($\alpha$-hydroxy acids), calcium-phosphates (CaP) (such as $\beta$-tricalcium phosphate ($\beta$-TCP) and $\alpha$-tricalcium phosphate ($\alpha$-TCP)), poly(D,L-lactide) (PDLLA), injectable bone (for example, injectable bone that includes calcium phosphate and/or calcium sulphate), allotransplantation (i.e., bone and/or tissue from a same species, such as allografts and autografts), xenotransplantation (i.e., bone and/or tissue from another species), rattan wood, bioactive glasses (such as a bioactive glass foam scaffold), cancellous structured titanium, resorbable porous structures, class A and class B bioactive materials, bone grafts, and other materials that cause and/or stimulate bone growth.

Furthermore, the substance can be formed with various geometric configurations, such as including one or more of a liquid, a powder, and/or a solid. These configurations include both porous structures and non-porous structures. Further yet, these configurations include the substance being formed to have a three-dimensional solid structure, such as a scaffold or scaffolding, a porous structure, a structure that imitates cancellous bone, a structure that imitates cortical bone, a mesh, and/or a solid platform that provides a framework for the support and growth of bone. By way of example, the substance is formed into a three-dimensional porous scaffold and placed in the internal cavity (for example, PGA, PLA, and/or PLGA scaffolds). The pore size and porosity of the scaffold can be optimized to induce colonization and proliferation of cells. For example, the pore sizes range from about 150 μm-700 μm), and the porosity of the scaffold ranges from about fifty percent (50%) to ninety percent (90%).

As discussed herein, the porous structure of the substance and/or the bone fixation body can be formed from a variety of different materials and different processes. As one example, the porous structure is formed from one or more of polymers, ceramics, and biocompatible metals and metal alloys. For example, the porous structure is constructed with tantalum, titanium, a titanium (Ti) alloy, such as titanium with one or more of zirconium (Zr), niobium (Nb), tin (Sn), silicon (Si), molybdenum (Mo), and tantalum (Ta)), biocompatible polymer, and/or a biocompatible metal or metal alloy.

By way of example, the porous structure is formed from one of a casting process and/or a powder metallurgy process. The casting process can include one or more of vacuum melting and annealing, hot rolling, scale removal, machining, and surface preparation. The powder metallurgy process can include one or more of a pre-alloying process (such as fabricating alloyed powder using gas atomization and melting) and a blending of metals to obtain a predetermined alloy composition. Metal powder is then cold pressed into a shaped and sintered. The porous structure can also be fabricated using one or more of sintering, casting, plasma-spraying, sputter deposition techniques, and metallic deposition techniques.

As another example, the porous structure is formed by coating a solid skeleton or a hollow skeleton with one or more of a polymer, a metal, and/or a metal alloy. For example, a carbon skeleton is coated with tantalum using a vapor deposition process. For instance, tantalum is deposited on a vitreous carbon foam structure.

As yet another example, the porous structure is formed from a metal injection molding (MIM) process. For example, metals and/or polymers are mixed to form a feedstock that is then shaped. The polymer is then removed, and the structure is heated, machined, and coated.

Furthermore, the porous structure can include opens cells (i.e., pores connected to each other through channels, voids, interstices, etc.), closed cells (i.e., pores disconnected from each other), and combinations of open and closed cells.

Additionally, the porosity of the porous structure can be constant throughout the porous structure or change within the porous structure. For instance, the porous structure can have a gradient porosity in which the porosity changes from the surface of the bone fixation body to the center of the bone fixation body (for example, the porosity near the surface of the bone fixation body is different than the porosity inside the internal cavity).

The porosity can also increase or decrease at different locations along the hip implant. For instance, the porosity of the porous structure where the bone fixation body contacts cortical bone can be different than the porosity where the bone fixation body contacts cancellous bone. The porosity of the porous structure where the hip implant contacts cortical bone can be lower than the porosity of the porous structure where the hip implant contacts cancellous bone. Looking to FIG. 10B for example, the bone fixation body 116 at or adjacent the proximal end 140 where the hip implant 100 contacts cortical bone has a different porosity than where the bone fixation body 116 contacts cancellous bone at or adjacent the distal end 142. Thus, the bone fixation body can have a first porosity at the proximal end and a second, different porosity at other locations, such as near or at the distal end.

Although illustrative embodiments have been shown and described, a wide range of modifications, changes, and substitutions is contemplated in the foregoing disclosure; and some features of the embodiments may be employed without a corresponding use of other features. Accordingly, it is appropriate that the appended claims be construed broadly and in a manner consistent with the scope of the embodiments disclosed herein.

What is claimed is:

1. A method, comprising:
  machining a neck body of a hip implant from solid metal to include a neck portion with a cylindrical configuration that receives a femoral ball at a proximal end of the neck body, a flat end surface at a distal end of the neck body, and a male protrusion that extends away from the flat end surface at the distal end of the neck body such that the male protrusion has an elongated shape that tapers while extending from the flat end surface at the distal end of the neck body to a distal end of the male protrusion and such that the male protrusion includes a non-circular shape in a cross-sectional view;
  heating a biocompatible material in a furnace that fabricates a bone fixation body formed of a porous metal structure that has a tapering body that extends in a side view from a flat end surface at a proximal end of the bone fixation body to a distal end of the bone fixation body, has an external bow on one side in the side view, has a trapezoidal shape in a cross-sectional view, and has the porous metal structure that extends throughout the bone fixation body such that the porous metal structure includes a geometric configuration with a size and a shape of cancellous human bone; and
  heating the bone fixation body and the neck body so that the bone fixation body permanently bonds around the neck body to form the hip implant such that the male protrusion extends into and forms a solid metal core for the bone fixation body, the flat end surface at the proximal end of the bone fixation body bonds at a junction to the flat end surface at the distal end of the neck body, and the bone fixation body and the neck body bond to provide anti-rotation at an interface where the bone fixation body bonds to the non-circular shape of the male protrusion.

2. The method of claim 1, wherein the bone fixation body simultaneously bonds to the neck body during fabrication of the bone fixation body.

3. The method of claim 1, wherein the bone fixation body bonds to the neck body after the bone fixation body is separately fabricated from the neck body.

4. The method of claim 1 further comprising:
  fabricating the porous metal structure such that a depth of bone growth is not restricted to a thin porous coating but bone grows and integrates into the porous metal structure.

5. The method of claim 1, wherein a porosity of the porous metal structure includes a portion with a porosity of 65%.

6. The method of claim 1, wherein the bone fixation body is fabricated so the bone fixation body does not include a solid metal substrate.

7. The method of claim 1, wherein an average pore diameter of the porous metal structure is 40 μm to 800 μm.

8. The method of claim 1, wherein the bone fixation body is heated in the furnace and formed to have a shape and a contour of a human intramedullary canal in order to fit into the human intramedullary canal and conform to anatomical contours of a human patient.

9. A method, comprising:
  machining solid metal to form a neck body of a hip implant that includes a neck portion at a proximal end of the neck body with a cylindrical configuration that receives a femoral ball and that includes a flat end surface at a distal end of the neck body such that a male protrusion extends outwardly from the flat end surface at the distal end of the neck body and the male protrusion tapers while extending from the flat end surface at the distal end of the neck body to a distal end of the male protrusion and includes a non-circle shape in a cross-sectional view;

heating a biocompatible material in a furnace that forms a porous metal structure that is a bone fixation body of the hip implant such that the porous metal structure formed in the furnace: includes a trapezoidal shape in a cross-sectional view, extends from a flat end surface at a proximal end of the bone fixation body to a distal end of the bone fixation body, has a tapering body that tapers from the flat end surface at the proximal end of the bone fixation body to the distal end of the bone fixation body, has an external bow on one side as seen in a side view of the hip implant, and is formed of porous metal that extends throughout the bone fixation body with the porous metal having a geometric configuration with a size and a shape of cancellous human bone such that the porous metal encourages the cancellous human bone to migrate and grow into the bone fixation body; and heating the bone fixation body and the neck body to bond the bone fixation body around the neck body to form the hip implant such that the bone fixation body bonds to the neck body along an interface that includes a junction where the flat end surface at the proximal end of the bone fixation body bonds to the flat end surface at the distal end of the neck body and includes a portion of the male protrusion that tapers and includes the non-circular shape of the male protrusion that extends into the bone fixation body and forms a solid metal core for the bone fixation body.

10. The method of claim 9, wherein the bone fixation body simultaneously forms and attaches to the neck body.

11. The method of claim 9, wherein the bone fixation body and the neck body are fabricated independently and subsequently bonded together.

12. The method of claim 9, wherein the porous metal structured is formed in the furnace to have a shape of a human intramedullary canal in order to fit into the human intramedullary canal and conform to anatomical contours of a human patient.

13. The method of claim 9, wherein the porous metal structure includes an average pore diameter between 40 µm to 800 µm and includes a porosity with a value of 65%.

14. A method, comprising:
machining solid metal to form a neck body of a hip implant to have a proximal end with a neck portion with a cylindrical configuration that receives a femoral ball, to have a distal end with a flat end surface, and to have a male protrusion that extends outwardly from the flat end surface at the distal end of the neck body and that tapers while extending from the flat end surface at the distal end of the neck body to a distal end of the male protrusion and that includes a non-circular shape in a cross-sectional view;

heating a biocompatible material in a furnace to fabricate a porous metal structure that is a bone fixation body of the hip implant so that the porous metal structure is formed in the furnace to: extend from a flat end surface at a proximal end of the bone fixation body to a distal end of the bone fixation body, include a trapezoidal shape in a cross-sectional view, include a tapering body that tapers from the flat end surface at the proximal end of the bone fixation body to the distal end of the bone fixation body, include an external bow on one side as seen in a side view of the hip implant, be formed without a solid metal substrate, and be formed of porous metal that extends throughout the bone fixation body and that has a geometric configuration with a size and a shape of cancellous natural human bone in order to encourage bone to migrate and grow into the porous metal structure that is the bone fixation body; and heating the bone fixation body and the neck body so the bone fixation body bonds around the neck body to form the hip implant such that the male protrusion forms a solid metal core for the bone fixation body, the flat end surface at the proximal end of the bone fixation body bonds at a junction to the flat end surface at the distal end of the neck body, and the neck body and the bone fixation body bond along an anti-rotation interface that includes where the non-circular shape of the male protrusion bonds to the bone fixation body.

15. The method of claim 14, wherein the bone fixation body simultaneously forms and attaches to the neck body.

16. The method of claim 14, wherein the bone fixation body and the neck body are fabricated independently and subsequently bonded together.

17. The method of claim 14, wherein the porous metal structure forms in the furnace to have a shape of a human intramedullary canal in order to fit into the human intramedullary canal and conform to anatomical contours of a human patient.

* * * * *